United States Patent [19]

Dunski

[11] Patent Number: 4,727,103

[45] Date of Patent: Feb. 23, 1988

[54] ISOCYANURATE ESTERS OF CARBOXYALKYLTHIOALKANOESTER-PHENOL COMPOUNDS AND POLYOLEFIN POLYMERIC COMPOSITIONS STABILIZED THEREWITH

[75] Inventor: Neil Dunski, Creve Coeur, Mo.

[73] Assignee: Mallinckrodt, Inc., St. Louis, Mo.

[21] Appl. No.: 68,010

[22] Filed: Jun. 29, 1987

[51] Int. Cl.$^4$ .................. C07D 251/30; C07D 251/32; C08K 5/13; C08K 5/24

[52] U.S. Cl. .................................... 524/101; 524/291; 524/302; 524/304; 524/305; 544/221

[58] Field of Search ................ 544/221; 524/101, 291, 524/302, 304, 305

[56] References Cited

U.S. PATENT DOCUMENTS 4,569,959  2/1986  Dunski et al. ...................... 544/221
4,633,008  12/1986  Oonishi et al. ...................... 544/221

Primary Examiner—Henry R. Jiles
Assistant Examiner—J. G. Mullins
Attorney, Agent, or Firm—R. J. Klostermann; L. N. Goodwin; V. Peoples, Jr.

[57] ABSTRACT

Isocyanurate esters of carboxyalkylthioalkanoesterphenols useful in the stabilization of organic materials normally susceptible to oxidative degradation are prepared by reacting an appropriate isocyanurate trithiol, which is a selected tris-mercapto alkanoic acid ester of tris-(2-hydroxyethyl) isocyanurate with an appropriate alkenyl compound, which is a selected 4-hydroxy-(mono- or di-alkyl)phenyl alkyl alkenoate. In a preferred embodiment, the ester is 1,3,5-tris [( 3,5-di-tert-butyl-4-hydroxyphenyl)-(3-propyl) oxycarbonylethylthiopropionyloxyethyl] isocyanurate.

9 Claims, No Drawings

ISOCYANURATE ESTERS OF CARBOXYALKYLTHIOALKANOESTERPHENOL COMPOUNDS AND POLYOLEFIN POLYMERIC COMPOSITIONS STABILIZED THEREWITH

This invention relates to isocyanurate esters of carboxyalkylthioalkanoesterphenols useful in the stabilization of organic materials normally susceptible to oxidative degradation, a process for preparing the compounds and organic material stabilized with the compounds.

Numerous compounds, including various sterically hindered phenol derivatives, have been proposed for stabilizing organic materials, such as organic polymers, against oxidative and thermal degradation.

Knell et al, U.S. Pat. No. 3,679,744, discloses thiodialkanoamidophenol compounds (more specifically designated as N,N'-bis(alkylhydroxyphenyl)thiaalkanedicarboxamides) obtained by a procedure involving the reaction of a selected alkylaminophenol with a thiodialkanoyl chloride. According to the patent, these monosulfur compounds are useful as stabilizers of organic materials which are subject to oxidative deterioration. Poly-alpha-olefins such as polyethylene, polypropylene, polybutylene, polyisoprene and copolymers thereof are included among the organic materials set forth in the patent. One such monosulfur compound, disclosed in Example I thereof, is N,N'-bis(3',5'-di-t-butyl-4'-hydroxyphenyl)2-thiapropane-1,3-dicarboxamide.

Gilles, U.S. Pat. No. 3,531,483, discloses hydroxyphenylakyleneyl isocyanurates as stabilizers for organic materials. One such compound disclosed therein is tris-(3,5-di-tert-butyl-4-hydroxybenzyl) isocyanurate.

Nakahara et al, U.S. Pat. No. 4,226,991, discloses a process for preparing a polyhydric alcohol 3-alkylthiopropionate polyolefin resin stabilizer. One such compound disclosed therein is 1,3,5-tris-(n-hexylthiopropionyloxyethyl) isocyanurate.

Steinberg et al., U.S. Pat. No. 3,707,542, discloses esters of tris-(hydroxyalkyl) isocyanurates with dialkyl-4-hydroxyphenyl carboxylic acids as stabilizers of organic materials. One such compound disclosed therein is tris-(2-[3-(3,5-di-tert-butyl-4-hydroxyphenyl)propionyloxy]ethyl) isocyanurate.

Beears, U.S. Pat. No. 3,742,032 discloses hexahydro-1,3,5-tris-[beta-(alkylcarboxyalkylthio)propionyl]-s-triazines as stabilizers for polyolefins, particularly polyethylene and polypropylene. One such compound disclosed therein is hexahydro-1,3,5-tris-[beta-(n-dodecyl-2-carboxyethylthio)propionyl]-s-triazine.

However, heretofore known compounds, such as the compounds set forth above, have not been entirely satisfactory for stabilizing organic materials, such as polyolefins (e.g., polyethylene and polypropylene) against oxidative and thermal degradation. Accordingly, there is a substantial need in the art for new compounds having the capability of stabilizing organic materials such as polyethylene and polypropylene against such degradation.

Dunski U.S. Pat. No. 4,569,959 and its continuation-in-part application now pending as U.S. Ser. No. 827,988 discloses isocyanurate esters of thioamidophenols and polyolefin polymeric compositions stabilized therewith.

It has now been found that the hereinafter described isocyanurate esters of carboxyalkylthioalkanoesterphenol have stabilizing capabilities. Such compounds are hereinafter sometimes referred to as Compound C or terms of similar import.

DESCRIPTION OF THE INVENTION

Generally stated, the present invention provides Compound C compounds which may be represented by Formula I below:

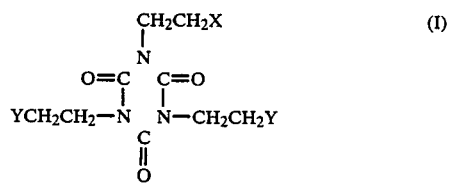

Where Y is a monovalent group represented by Formula II below:

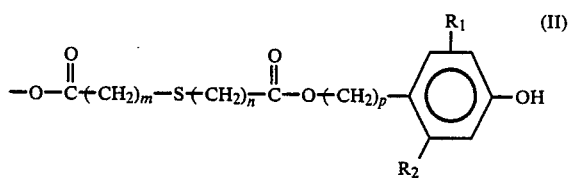

wherein $R_1$ is an alkyl group containing from one to eight carbon atoms or a cycloalkyl group containing from five to 12 carbons atoms; $R_2$ is hydrogen, an alkyl group containing from one to 8 carbon atoms or a cycloalkyl group containing from 5 to 12 carbon atoms; and m is an independently selected integers from 1 to about 10 and n is an independently selected integer from 1 to about 14, and p is an independently selected integer from 1 to about 8, preferably 3, and X is y or —OH, preferably X is y.

In still another aspect of this invention, there are provided organic compositions of matter stabilized against thermal-oxidative degradation, which comprise an organic material and a stabilizing amount of the compound of Formula I.

DETAILED DESCRIPTION OF THE INVENTION AND OF THE MANNER AND PROCESS OF MAKING AND USING IT

In the compounds of Formula II above where $R_2$ is other than hydrogen, in general each $R_2$ substituent is preferably located ortho to the hydroxyl group on its respective benzene ring, but may be in the meta position.

Suitable alkyl groups from which $R_1$ and $R_2$ may be selected include methyl, ethyl, propyl, isopropyl, butyl, amyl, hexyl, octyl, and the like. Included also are tertiary alkyl groups, such as t-butyl, t-amyl, t-octyl, and the like. Suitable cycloalkyl groups from which $R_1$ and $R_2$ may be selected include cyclopentyl, cyclohexyl, cyclooctyl, cyclododecyl, and the like. Preferably, $R_1$ and $R_2$ are t-butyl groups, with both $R_2$ groups located in their ortho positions. The number of $CH_2$ groups in the compounds is preferably such that each of m and n is 2 and each p is 3 in Formula II above.

The Compound C compound of this invention includes, for example:

(a) 1,3,5-tris [(3,5-di-tert-butyl-4-hydroxyphenyl) (3-propyl)oxycarbonylethylthiopropionyloxyethyl]isocyanurate (b) 1,3,5-tris [(3,5-di-tert-butyl-4-hydroxyphenyl)(3-propyl)oxycarbonylethylthioacetyloxyethyl-]isocyanurate (c) 1,3,5-tris [(3,5-di-tert-butyl-4-hydroxyphenyl) (3-propyl)oxycarbonylpropylthiopropionyloxyethyl-]isocyanurate (d) 1,3,5-tris [(3-tert-butyl-4-hydroxyphenyl) (3-propyl)oxycarbonylethylthiopropionyloxyethyl-]isocyanurate (e) 1,3,5-tris [(3-tert-butyl-5-methyl-4-hydroxyphenyl) (3-propyl)oxycarbonylethylthiopropionyloxyethyl]isocyanurate Preferred compounds of this invention are compounds (a) and (b) above. Compound (a) above is most preferred and corresponds to Formula I above where X is Y and Y is represented by Formula III as follows:

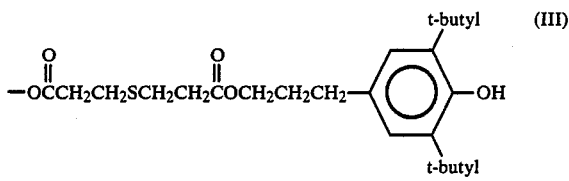

The Compound C compounds of this invention can be prepared by reaction of isocyanurate trithiols with alkenes. The reaction is carried out by reacting an appropriate isocyanurate trithiol, i.e. 1,3,5-tris(2-ethyl-3-mercaptopropionate) isocyanurate with 3-(3,5-di-tert-butyl-4-hydroxyphenyl) propylacrylate.

The reaction is carried out preferably without a solvent since the reactants form a liquid mixture. However, the reaction can be carried out in a solution containing the reactants and at least a solubilizing amount of an inert solvent for at least one, and preferably both, of the reactants and a basic catalyst. Chloroform is preferred as the solvent. When n in formula II is 2, the catalyst can be an alkali metal alkoxide such as sodium methoxide or quarternary ammonium hydroxide such as trimethylbenzyl ammonium hydroxide (preferred), which is commercially available under the trademark Triton B (Rohm & Haas Co.). When n in formula III is 3 or more, a free radical generator such as a peroxide or an azonitrile preferably azobisisobutyronitrile is used. The catalyst is preferably employed in an amount of about 0.05 gram-mole per one gram-equivalent of available—SH groups of the isocyanurate trithiol.

The reaction may be carried out at any suitable temperature, e.g., about 20°–25° C., and any suitable pressure, e.g., 760 mm Hg, for any suitable period, e.g., from about 0.5 to about 20 hours or more. Although the time required for completion of the reaction is dependent upon the particular reactants and concentrations thereof, catalyst and concentration thereof, solvent, temperature, and pressure employed, the reaction will, in general, be substantially complete within about 1 to about 10 hours.

Advantageously, the reaction is carried out with stirring and under an inert gaseous blanket, i.e., at least substantially inert to the reactants, catalyst, solvent and products employed. Nitrogen is the preferred inert gaseous blanket.

The isocyanurate trithiols for use in the above thiol-alkene reaction can be prepared from tris-(2-hydroxyethyl) isocyanurate and appropriate mercaptoalkanoic acids by well known methods such as the general method set forth in Los, U.S. Pat. No. 3,676,440. The alkenes for use in such reaction can be prepared by esterification of appropriate $C_2$–$C_{15}$ alkenoyl acid halides containing terminal ene functionality, e.g., acrylic and chloride, with the appropriate 4-hydroxy-(mono- or di-alkyl) phenylalkanol.

The thiol-alkene reaction set forth above can be (and preferably is) used to prepare those Compound C compounds of this invention where n in Formula II above is 2 to 14. However, where n is 1, this reaction is inapplicable.

The compounds of the present invention are useful as stabilizers of organic materials normally subject to oxidative deterioration. Such organic materials include, for example: synthetic organic polymeric substances such as vinyl resins formed from the polymerization of vinyl halides or from the copolymerization of vinyl halides with unsaturated polymerizable compounds, e.g., vinyl esters, alpha-beta-unsaturated aldehydes and unsaturated hydrocarbons such as butadienes and styrene; poly-alpha-olefins such as polyethylene (e.g., linear low density polyethylene), polypropylene, polybutylene (e.g., polybutene-1), polyisoprene, and the like, including copolymers of poly- alpha-olefins, polyurethanes, polyamides such as polyhexamethylene adipamide and polycaprolactam; polyesters such as polymethylene terephthalates; polycarbonates, polyacetals; polystyrene; polyethyleneoxide; and copolymers such as those of high impact polystyrene containing copolymers of butadiene and styrene and those formed by the copolymerization of acrylonitrile, butadiene and/or styrene. Other materials which can be stabilized by the active compounds of the present invention include lubrication oil of the aliphatic ester type, i.e., di(2-ethylhexyl)-azelate, pentaerythritol tetracaproate, and the like; animal and vegetable derived oils, e.g., linseed oil, fat, tallow, lard, peanut oil, cod liver oil, castor oil, palm oil, corn oil, cotton-seed oil, and the like; hydrocarbon materials such as gasoline, mineral oil, fuel oil, drying oil, cutting fluids, waxes, resins and the like, fatty acids, soaps and the like.

The compounds of this invention (represented by Formula I above) may be employed in any stabilizing amount as stabilizers for organic materials normally susceptible to oxidative degradation. Such amount may be for example, from about 0.005% to about 10% by weight of the stabilized composition. For polyolefins, e.g., linear low density polyethylene, polypropylene and poly(butene-1), such amount is preferably from about 0.05% to about 5% and more preferably from about 0.1% to about 1%.

The compounds of this invention may be used alone or in combination with other stabilizers or additive materials, such as dilauryl-beta-thiodipropionate and distearyl-beta-thiodipropionate.

Other antioxidants, antiozonants, thermal stabilizers, ultraviolet light absorbers, coloring materials, dyes, pigments, metal chelating agents, etc. may also be used in the compositions of the invention.

Phosphite esters may also be used in stabilized compositions containing the novel antioxidant compounds of the present invention. Such phosphite esters include dialkyl phosphites (for example, distearyl phosphite, dilauryl phosphite, and the like e.g., trialkyl phosphites (for example, trilauryl phosphite, tris(ethylhexyl) phosphite, and the like); and tris(alkaryl) phosphites (for example tris(nonylphenyl)phosphites, and the like).

The compounds of this invention are especially useful for stabilizing polymeric materials such as polyolefins and the like, e.g., polyethylene (especially linear low density polyethylene, i.e., LLDPE), polypropylene, poly(butene-1), and the like.

Stabilized compositions of matter of this invention may be prepared by incorporating the compounds into the organic material to be stabilized using well known methods for incorporating stabilizers into such material. For example, in general, the stabilizer may simply be physically admixed with the organic material.

It is well known that upon processing polyethylenes at elevated temperature, cross-linking takes place. This results in an apparent increase in molecular weight and hence lower melt index values. More importantly, it also results in a change in molecular weight distribution by increasing, due to cross-linking the high molecular weight tail. In many applications, it is desired that polyethylene not cross-link while being processed. Accordingly, a feature of a good stabilizer is that the melt index does not appreciably decrease when working a polyethylene as in extrusion operations.

In contrast to polyethylenes, polypropylene typically undergoes chain scission during processing thereof at elevated temperatures, i.e., a reduction in apparent molecular weight. This is reflected typically in melt flow rate values which increase as the molecular weight decreases.

Practice of the present invention is illustrated by the following non-limiting examples. All parts, percents and other amounts given throughout this disclosure, including the examples which follow, are by weight unless otherwise indicated.

EXAMPLE 1

Tris-(2-hydroxyethyl) Isocyanurate:

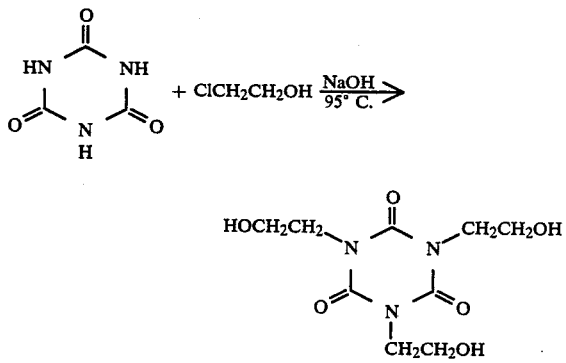

This starting material, tris-(2-hydroxyethyl) isocyanurate, was prepared in 80% yield according to the procedure by Sayigh and Ulrich described in J. Chem. Soc., 1961 p. 3148. The white crystalline product has a melting point of 133°-135° C.

The above material is used as the nucleus for Compound C.

EXAMPLE 2

(Compound C)

Tris-(2-hydroxyethyl) isocyanurate (13.05 g, 0.05M) and 3-mercaptopropionic acid (15.9 g, 0.15M) in 150 ml of toluene were charged into a 500 ml 3-neck flask and heated to reflux with stirring under $N_2$ atmosphere in the presence of 0.2 g of p-toluenesulfonic acid monohydrate until the theoretical amount of water was collected in the Dean Stark trap. A mushy white solid m.p. 35° C., yield 90% was collected by filtration. The intermediate was identified as tris-(2-ethyl-3-mercaptopropionate) isocyanurate (1).

A mixture of the isocyanurate intermediate (1) [7.4 g, 0.014 mole] and 3'-(3,5-di-tert-butyl-4-hydroxyphenyl)-propyl acrylate (15.9 g, 0.05 mole) were vigorously stirred in the presence of 0.2 g of sodium methoxide. The mixture was allowed to stir overnight at room temperature. The thick deep yellow mixture was dissolved in 40 ml of toluene and washed successively with 5% HCl solution, saturated solution of sodium bicarbonate followed by a saturated solution of sodium chloride. Evaporation of the solvent after drying over anhydrous $MgSO_4$ left a light yellow liquid in quantitative yield. The structure was confirmed as 1,3,5-tris[(3,5,-di-tert-butyl-4-hydroxyphenyl)-(3-propyl)oxycarbonylethylthiopropionyloxyethyl]isocyanurate on the basis of IR, $^1H$ and $^{13}C$ NMR spectroscopic techniques.

(COMPOUND C)

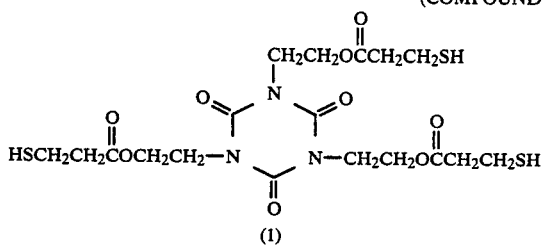

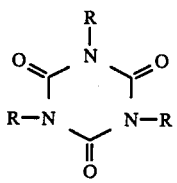

R =

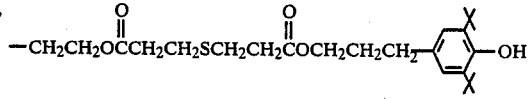

EXAMPLE 3

EVALUATION RESULTS IN LINEAR LOW DENSITY POLYETHYLENE (LLDPE)

The LLDPE employed in our evaluation was the precursor to Union Carbide G-Resin 7047 Natural 7 antioxidant modified linear low density polyethylene resin, i.e. such resin prior to incorporating an antioxidant. This copolymer typically has a density of of 0.92, a melt index of about 1.0 (ASTM D1238 condition E) and 1-butene comonomer content of about 3-5 mole percent.

A dry blend was prepared by admixing at room temperature 1.0 g of the antioxidant and 200 g of resin in a Ronson blender. The blender was operating at speed 10 for 3 minutes. The concentrate was transferred to a polyethylene bag and additional 800 g of resin added and blended in the bag.

The blend was then extruded on a ¾" Brabender extruder at 50 rpm with all 4 zones set at 210° C. The extruded rod was water quenched, dried and pelletized. The procedure was repeated five times at 50 rpm and 260° C. Pellet samples were retained following each extrusion to determine melt index. The same procedure was repeated on LLDPE resin not containing an antioxidant.

The following results were obtained:

| | Melt Index, g./10 min. ASTM D1238 E | | |
|---|---|---|---|
| Compound | Pass #1 at 260° C. | Pass #3 at 260° C. | Pass #5 at 260° C. |
| Blank (Unstabilized) | 0.61 | 0.38 | 0.29 |
| Compound C | 0.90 | 0.83 | 0.71 |

EXAMPLE 4

Pellet samples removed following the extrusion at 210° C. were compression molded at 170° C. and 3500 psi into 15 mil thick plaques. Twelve chips, each about 1 inch in diameter, were cut from each plaque and placed in a 150° C. air circulating oven. Time to degradation was determined for these chips as shown below:

| Antioxidant | Hours to Degradation at 150° C. |
|---|---|
| Blank | 24 |
| Compound C | 144 |

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. An ethyl isocyanurate carboxyalkylthioalkanoesterphenol compound having the following Formula I:

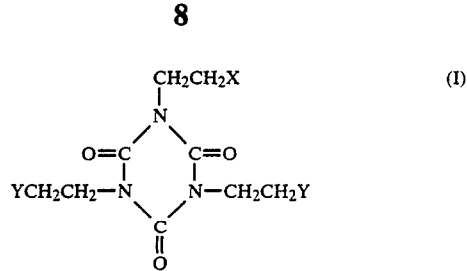

where Y is a monovalent group having the following Formula II:

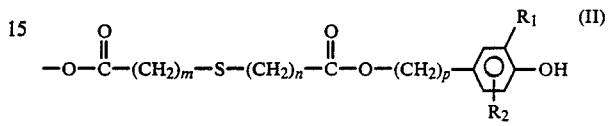

where $R_1$ is an alkyl group containing from 1 to 8 carbon atoms or a cycloalkyl group containing from 5 to 12 carbon atoms; $R_2$ is hydrogen, an alkyl group containing from 1 to 8 carbon atoms or a cycloalkyl group containing from 5 to 12 carbon atoms; m is a selected integer from 1 to about 10, and n is a selected integer from 1 to about 14, and p is a selected integer from 1 to about 8; and X is Y or —OH.

2. The compound of claim 1 wherein $R_1$ and $R_2$ are tertiary alkyl groups.

3. The compound of claim 1 wherein $R_1$ and $R_2$ are tertiary butyl groups.

4. The compound of claim 1 where p is 3.

5. The compound of claim 1: 1,3, 5-tris[(3,5-di-tert-butyl-4-hydroxyphenyl)-(3-propyl) oxycarbonylethylthiopropionyloxyethyl]isocyanurate.

6. The compound of claim 1: 1,3,5-tris [(3,5-di-tert-butyl-4-hydroxyphenyl)-(3-propyl) oxycarbonylethylthioacetyloxyethyl] isocyanurate.

7. A composition of matter comprising a polyolefin normally subjected to oxidative deterioration and a stabilizing amount of the compound of claim 1, 2, 3, 4 or 5.

8. A composition of matter comprising linear low density polyethylene and a stabilizing amount of the compound of claim 1, 2, 3, 4 or 5.

9. A composition of matter comprising polypropylene and a stabilizing amount of the compound of claim 1, 2, 3, 4 or 5.

* * * * *